United States Patent [19]

Danby et al.

[11] Patent Number: 4,601,294
[45] Date of Patent: Jul. 22, 1986

[54] EAR CANAL ELECTRODE

[75] Inventors: Hal C. Danby, Palo Alto; Myron A. Beigler, Los Altos Hills, both of Calif.

[73] Assignee: Minnesota Mining and Manufacturing Company, St. Paul, Minn.

[21] Appl. No.: 424,425

[22] Filed: Sep. 27, 1982

Related U.S. Application Data

[63] Continuation-in-part of Ser. No. 342,490, Jan. 25, 1982, abandoned.

[51] Int. Cl.$^4$ ............................ A61B 5/12; A61B 5/04
[52] U.S. Cl. ...................................... 128/642; 128/746
[58] Field of Search ........ 128/639, 642, 746, 151–152, 128/341, 343, 9; 181/129–130, 135; 179/107 E

[56] References Cited

U.S. PATENT DOCUMENTS 4,073,287  2/1978  Bradley et al. ............... 128/642
4,122,841 10/1978  Rock et al. ................... 128/746

OTHER PUBLICATIONS

Lundborg, T. et al, *Scandinavian Auditory Supplementum No.* 13, (1981), pp. 55–64.
Erickson, D. et al, *Hearing Instruments*, (1981), pp. 34–43.

Primary Examiner—Kyle L. Howell
Assistant Examiner—Angela D. Sykes
Attorney, Agent, or Firm—Donald M. Sell; James A. Smith; William D. Bauer

[57] ABSTRACT

A non-invasive, external ear canal electrode useful for transmitting sound stimulus to an ear canal and for conducting electrical signals picked up from the ear canal epidermal surface comprising an electroconductive tube having a resilient annnular sensor comprising a silver conductor attached to the end to be placed in the ear.

24 Claims, 8 Drawing Figures

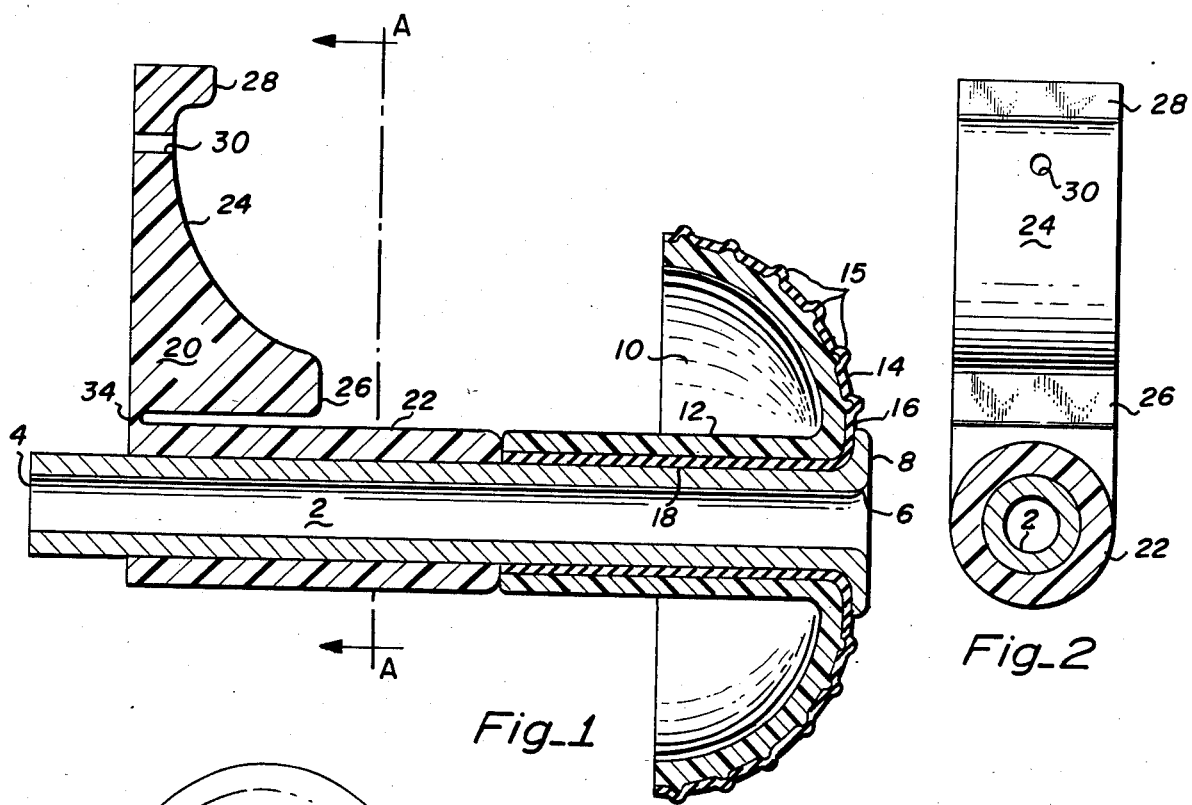
Fig_1
Fig_2
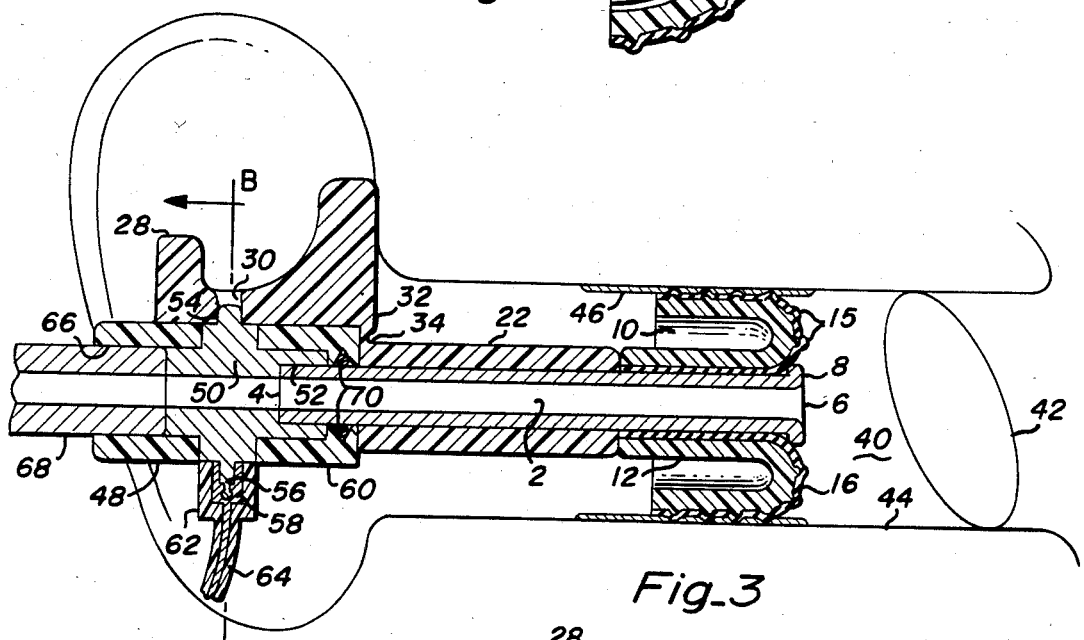
Fig_3
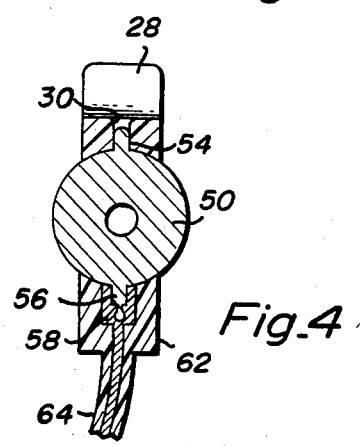
Fig_4

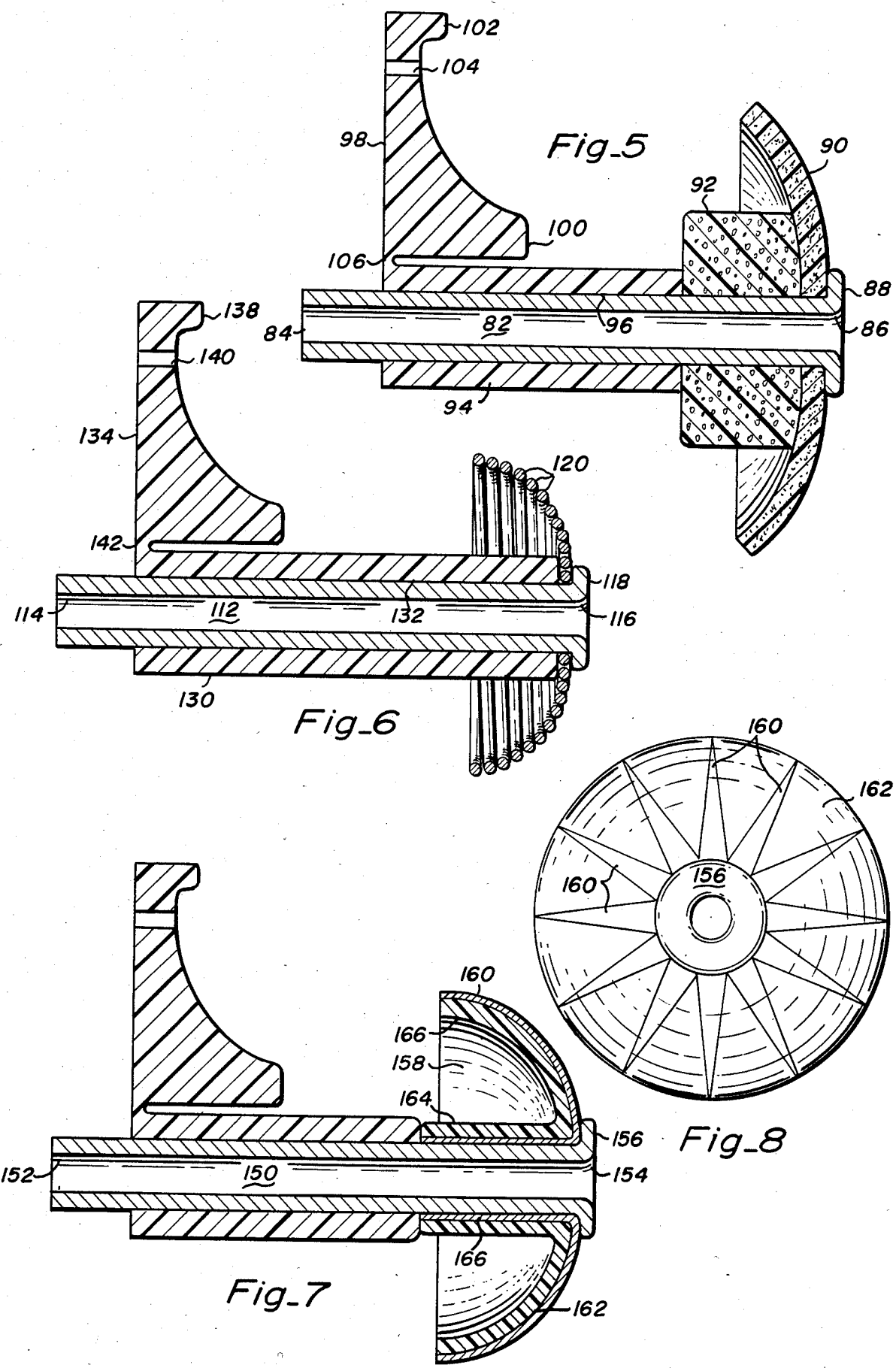

EAR CANAL ELECTRODE

REFERENCES TO RELATED APPLICATIONS

This application is a continuation-in-part of application Ser. No. 342,490, filed Jan. 25, 1982 and now abandoned.

FIELD OF THE INVENTION

This invention relates to improved devices for identifying and diagnosing hearing defects using auditory stimulation and auditory brainstem response measurements.

BACKGROUND OF THE INVENTION

Medical examinations to identify and diagnose hearing defects have historically involved physical examination of the ear canal and observing the subjective response to sound stimulus. Generally, the subjective sensitivity to volume has been routinely measured at several auditory frequencies. Most recently, the evoked action potentials resulting from auditory stimulation and auditory brainstem responses have been measured in an effort to identify more specifically the cause and degree of hearing loss and other hearing defects. Auditory brainstem response measurements involve auditory stimulation and measurement of the magnitude and response time of electrical signals originating from the otic nerve and brainstem in response to the auditory stimulus. The electrical signals are detected by using non-invasive electrodes mounted on the skin surface.

DESCRIPTION OF THE PRIOR ART

Ear canal mounted devices for providing auditory stimuli to the ear are well known in the art. The sound is frequently transmitted to the ear through a tubular component as shown in U.S. Pat. No. Re. 26,174 which is directed to a hearing aid and a method for its construction. In general, these devices are designed to provide a close or snug fit in the ear canal and may include resilient components to achieve this. U.S. Pat. No. 3,783,201 discloses a hearing aid with a flexible construction. U.S. Pat. No. 4,133,984 describes a hearing aid with a flexible, expandable (inflatable) end portion. These hearing aids are designed to provide auditory stimulus but are not suitable or intended to receive electrical signals from the surface of the ear canal.

Electrodes suitable for use in conducting electrical signals from the surface of the skin are commonly used in electrocardiology measurements and the like. These electrodes are designed to have a low resistance and high sensitivity as described in U.S. Pat. Nos. 3,547,104 and 4,166,453. The latter patent describes a body electrode comprising a porous foam disc impregnated with an electrically conductive gel and other components cooperating therewith made of electrical conductive plastic. These electrodes are designated to be easily applied to a flat skin surface. They are not suitable for ear canal insertion and are not adapted for providing any sound stimulus.

Conductive metal electrodes which penetrated the eardrum, i.e. transtympanic electrodes, have been used. They require use of an anesthetic, are painful and often result in infection. They have been used to pick up signals from close to the cochlea for increased signal strength of the first auditory action wave.

Typical electrodes designed for non-invasive external ear canal insertion for measuring auditory brainstem responses are described in *Scandinavian Audiology Supplementum No.* 13, titled "Scandinavian Symposium on Brain Stem" edited by T. Lundborg (Apr. 7-8, 1981). "Identification of Wave I by Means of Atraumatic Ear Canal Electrode" by Walter et al, pp 63-64 describes an electrode made of silver wire, the terminal end supporting a salt water impregnated cotton ball. "An Improved Technique for the Non-Invasive Recording of Brain-Stem Responses with a Specially Constructed Meatal Electrode" by Lang et al, pp 59-62 describe a silver wire electrode designed to be worn under earphones, the terminal end to be coated with electrode jelly. "Ear-canal Compared to Mastoid Electrode Placement in BRA" by Harder et al, pp 55-57 describes an acrylic plastic electrode with a silver element having a silver chloride surface layer embedded therein. Electrode paste is applied to the ear canal before inserting the electrode. These devices do not have the construction of the ear electrodes of this invention and do not provide the low resistance and high sensitivity thereof. Also, these devices have no means for providing auditory stimuli. In each referenced system, the auditory stimuli is provided through devices not physically associated with the ear electrode. An even greater limitation of all of the invasive and non-invasive electrodes of the prior art has been the requirement that a physician make the insertion because of the potential for inadvertent penetration of the eardrum.

OBJECTS AND SUMMARY OF THE INVENTION

It is an object of this invention to provide a non-invasive external ear canal electrode with decreased electrical resistance and greater electrical sensitivity.

It is a further object of this invention to provide a safe, disposable ear canal electrode which can be simply and inexpensively manufactured and which can be easily and safely inserted by medical assistants with a minimum amount of training in ear anatomy without the risk of eardrum damage due to inadvertent penetration thereof.

In summary, the safe and non-invasive external canal electrode of this invention comprises an electrode means comprising an electro-conductive metal for conducting electrical signals picked up from the ear canal surface. The electrode means has a proximal end and a distal end. The distal end has mounted thereon a resilient annular sensor, at least the outer surface of the annular sensor comprising a silver electroconductor.

The electroconductor is in electrical contact with the electrode means. The silver electroconductor can, for example, be a spiral coil or radial fan of silver wire or foil, a resilient conductive organic polymer having a silver filler, or preferably, a flared disk of resilient organic polymer having an outer conductive organic polymer coating with a silver filler. The tubular electrode means can constitute a means for transmitting a sound stimulus to an ear canal as well as functioning as a transmitter of electric signals picked up from the ear canal surface. The electrode has a guard or stop portion which limits the insertion distance in the ear canal short of the ear drum and has a fastener means for securely joining the electrode to auditory signal generator and electrical connectors which connect the electrode with other instrumentation used for analyzing auditory brainstem response (ABR).

BRIEF DESCRIPTION OF THE DRAWINGS

FIG. 1 is directed to a cross-sectional view of an ear canal electrode of this invention.

FIG. 2 is a cross-sectional view of the ear canal electrode shown in FIG. 1 taken along lines A—A.

FIG. 3 is a cross-sectional view of an ear canal electrode of this invention shown in FIG. 1 after insertion into the ear canal.

FIG. 4 is a cross-sectional view of the ear canal electrode shown in FIG. 3 taken along the lines B—B.

FIG. 5 is a cross-sectional view of another embodiment of ear canal electrode of this invention having a conductive metal filled elastomeric flange sensor.

FIG. 6 is a cross-sectional view of another embodiment of ear canal electrode of this invention having a metal wire coil sensor.

FIG. 7 is a cross-sectional view of still another embodiment of this invention having a silver foil sensor supported on an elastomeric flange.

FIG. 8 is an end view of the ear canal electrode shown in FIG. 7 showing the silver foil configuration.

DETAILED DESCRIPTION OF THE INVENTION

In an effort to diagnose the cause of partial and total hearing loss and other hearing defects, techniques have been developed around measurements of the auditory brainstem response (ABR) and electrocochleography (ECoG). The early techniques involved measuring electrical potential variations on the scalp surface within the first 10 milliseconds following auditory stimulation. The auditory system was stimulated with sound, usually in the form of short clicks or bursts of selected wave shape, amplitude and frequency. The resulting electrical field potentials generated by synoptic events and membrane potential fluctuations along the central auditory pathway, and in particular in the nerve cell layers of the deep brainstem structures, were transmitted through the volume (brain tissue, bone and extracellular fluid) of electrically conducting medium as potentials detected using the scalp electrodes. The amplitude and latency of the electrical potentials have been correlated with specific sites along the auditory nervous system pathway. Potentials originating from the cochlear transducer and auditory brainstem are the most significant. Irregularities in the amplitude and latency of the characteristic waves can be used to identify the degree and specific cause of a hearing deficiency.

A number of factors have limited the use of ABR and ECoG. Originally sharp clicks are distorted in passage and transmission in the ear passageways. The stimulus does not stimulate all of the cochlear hair cells simultaneously. Electrical potentials observed are very weak and often ambiguous due to distortion introduced by passage through the body structure and from background noise. Placements of electrodes in the ear canal and through the ear drum were found to reduce some distortion and give increased sensitivity. The surface of the ear canal is adjacent to dense, conductive bone, and electrical potentials measured on the ear canal surface have been transmitted through less insulative tissue and fluid. It was found that correctly designed metal, non-invasive ear canal surface electrodes can obtain signals equivalent to transtympanic electrodes. However, background noise was even greater in the ear with many non-invasive electrodes because of the configuration of the ear canal surface. Only with highly skilled investigators, elaborate skin surface preparation, expansion of the canal entrance with a speculum and insertion of electrodes with microsurgical forceps has resistance been measured below 10 Kohms.

The non-invasive external ear canal electrode of this invention, as set forth in more detail hereinafter, can be applied in a routine manner by ordinary, medically trained technicians to give an electrical resistance as low as one Kohm. This device also provides that sound is transmitted through an integral, acoustic horn with minimal distortion.

Referring to FIG. 1, a cross-sectional view of an ear canal electrode of this invention is shown. Tubular electrode 2 has a proximal end 4 and a distal end 6 which terminates in flange element 8. A resilient annular sensor 10 is mounted on the distal end 6 and includes a tubular portion 12 and a flange portion 14 which preferably flares back over the tubular portion 12. A conductive organic polymer coating 16 containing silver covers the outer surface of flange portion 14 and is continuous with the coating 18 covering the inner surface of the tubular portion 12. It is critical that the coating 16, 18 be unbroken to effect a secure electrical connection between coating 16 and the tubular electrode 2. Ridges 15 create an electrolytically conductive gel reservoir as explained in greater detail with regard to FIG. 3 hereinafter.

Connecting element 20 is mounted on tubular electrode 2 and includes tubular portion 22 through which tubular electrode 2 extends in frictional engagement. The connector 20 also includes a fastener portion 24 which has a safety stop portion 26, a tab 28 at the terminal end thereof for manually manipulating the fastener, and a hole 30 for receiving a latch projection.

FIG. 2 shows a cross-sectional view of the ear canal electrode shown in FIG. 1 taken along the lines A-A to illustrate the connector. The hole 30 is centrally located. The stop surface 32 butts the external ear surface as described in greater detail with regard to FIG. 3. Hinge area 34 has a reduced cross-sectional area to permit pivotal movement of the fastener portion 24 to the latching position shown in FIG. 3.

Referring to FIG. 3, a cross-sectional view of the ear electrode of this invention is shown in position in the ear. Ear canal 40 receives the electrode, the stop surface 32 preventing insertion to a distance which would make contact with the eardrum 42. The resilient annular sensor 10 bears against the epidermal surface 44 of the ear canal. An electrolytically conductive liquid or gel 46 insures optimum electric contact between the annular sensor 10 and the ear canal surface 44. The ribbed structures 15 create a gel reservoir insuring that a quantity of the electrolytically conductive gel remains between the surface 16 of the electroconductive coating and the epidermal surface 44 after insertion.

Connecting element 48 functions to connect the tubular electrode 2 to an auditory signal generator and an auditory brainstem response analyzer (not shown). The metal connector element 50 has a recess 52 for receiving and engaging the proximal electrode end 4. The recess 52 preferably has a mating or tang construction which forms a secure, noise-free connection between the element 50 and the outer surface of the electrode end 4. The connector element 50 is preferably made of the same metal as the metal of the tubular electrode 2 to minimize bimetal junction noise. The connector element 50 has a pin 54 which engages the hole 30 of the fastener and a connector pin 56 with which pin socket 58 engages. Insulating plastic portions 60 and 62 electrically insulate the connector element 50 and pin socket 58. Electrical conducting insulated wire 64 connects the pin socket 58 with the auditory brainstem response analyzer. The connecting element 48 has a recess 66 which sealingly engages an audiosignal conducting tube 68 from an auditory signal generator. Sealing ring 70 provides an air-tight seal between the connector 48 and the outer surface of the tubular element 2. Air leakage reduces the acuity of the audiosignal or "clicks" during passage of the sound waves through the tubular channel from the tube 68 to the ear canal 40.

FIG. 4 is a cross-sectional view of the ear canal electrode shown in FIG. 3 taken along lines B—B. It shows the connector element 50 in greater detail. Connector element 50 has a circular cross-section. The pins 54 and 56 can be integral with the connector element 50. Pin 54 can also be a separately formed pin secured to the connector element 50 by a suitable pin hole, adhesive bond, weld or the like.

The tubular electrode 2 can be made of metal, have a metal coating or outer layer, or be made of a conductive metal filled plastic. It is preferably made of silver or stainless steel or has an outer silver layer or coating. It can also be made of aluminum, copper, lead, lead-mercury amalgan, zinc and the like. The connector element 50 is preferably made of the same metal as the metal component of the outer surface of the proximal end 4.

The annular sensor 10 and the connector 20 are preferably made of a resilient organic polymer. Suitable organic polymers include elastic polymers such as plasticized polyvinyl chloride, polybutadiene, natural rubber, silicon rubbers, polyisoprene and the like. A preferred polymer is KRATON D, a thermoplastic elastomer styrene-butadiene-styrene polymer. The annular sensor 10 should be made of material having sufficient elastic strength to provide a secure but comfortable pressure against the inner surface of the ear canal electrode 44. The conductive coating 16 and 18 is made of a silver filled polymer such as described in U.S. Pat. Nos. 3,719,610 and 4,251,275, for example.

The electrolytically conductive medium 46 can be either a liquid gel, jelly or other dispersion having good electrolytically conducting properties. For example, the electrolytically conductive medium can be an electrically conductive emulsion comprising an emulsified material dispersed in an aqueous solution of a conductive salt such as sodium chloride, potassium chloride or sodium sulfate and a surfactant dispersing agent. It can be an electrically conducting jelly comprising an aqueous sodium chloride solution phase gelled with conventional gelling agents such as sodium carboxymethylcellulose and having as the conductive salt, potassium chloride, sodium sulfate, potassium sulfate, sodium bromide, potassium bromide, sodium nitrate, ammonium fluoride, ammonium bromide, ammonium nitrate, ammonium sulfate, and the like.

Referring to FIG. 5, a cross-sectional view of an alternate embodiment of an ear canal electrode of this invention is shown. Tubular electrode 82 has a proximal end 84 and a distal end 86 which terminates in conductive flange element 88. A resilient annular sensor 90 is mounted on the distal end 86 between the flange 88 and resilient annular foam member 92. Annular sensor 90 preferably flares back over the annular foam member 92. Annular sensor 90 is made of a conductive organic polymer containing metal and preferably silver particles or filaments in a conducting relationship. It is held in secure electrical connection with the tubular electrode 82 by flange element 88 and annular foam member 92.

Connecting element 94 is mounted on tubular electrode 82 and includes tubular portion 96 through which tubular electrode 82 extends in frictional engagement. The connector 94 also includes a fastener portion 98 which has a safety stop portion 100, a tab 102 at the terminal end thereof for manually manipulating the fastener, a hole 104 for receiving a latch projection, and a hinge portion 106.

The ear canal electrode shown in FIG. 5 is placed in the ear and connected to an auditory signal generator and an auditory brainstem response analyzer as described above with regard to the embodiment shown in FIG. 3. An electrolytically conductive medium such as a gel, for example, is placed in the ear canal or on the outer surface of the conductive flange element 90 to insure optimum electrical signal reception.

The tubular electrode 82 is preferably made of metal, coated with metal or is a plastic with a conductive metal filler. Suitable metals include aluminum, copper, silver, and the like. Preferred metals include stainless steel and silver. The annular sensor 90 is made of a silver particle or filament filled flexible organic polymer such as described in U.S. Pat. Nos. 3,976,600, 4,011,360, 4,093,563, or 4,113,981. The connector 94 and annular element 92 are made of non-conducting plastic and preferably made of a resilient organic polymer. Suitable organic polymers for connector 94 include elastic polymers such as plasticized polyvinyl chloride, polybutadiene, natural rubber, silicon rubbers, polyisoprene, styrene-butadiene-styrene polymers and the like. Annular element 92 is preferably a foam such as polyurethane foam, for example.

Referring to FIG. 6, a cross-sectional view of a still further embodiment of the ear canal electrode of this invention is shown. Tubular electrode 112 has a proximal end 114 and a distal end 116 which terminates in flange element 118. A resilient annular sensor 120 made of conductive metal wire and preferably silver wire in the form of a spiral is mounted on the distal end 116 and preferably flares back over the tubular portion 112. It should be in a secure electrical engagement with the tubular electrode 112.

Connecting element 130 is mounted on tubular electrode 112 and includes tubular portion 132 through which tubular electrode 112 extends in frictional engagement. The connector 130 also includes a fastener portion 134 which has a safety stop portion 136, a tab 138 at the terminal end thereof for manually manipulating the fastener, a hole 140 for receiving a latch projection, and a hinge portion 142.

The ear canal electrode shown in FIG. 6 is placed in the ear and connected to an auditory signal generator and an auditory brainstem response analyzer as described above with respect to FIG. 3. An electrolytically conductive medium such as a gel, for example, is placed in the ear canal before inserting the electrode to insure optimum, low resistance electrical signal pick-up. The electrode tube 112 and connector 130 are made of materials described in detail with regard to the corresponding components in the embodiment shown in FIG. 1, for example.

Referring to FIGS. 7 and 8, a further embodiment of the ear canal electrode of this invention is shown. Tubular electrode 150 has a proximal end 152 and a distal end 154 which terminates in flange element 156. A resilient sensor 158 has metal foil strips 160 (or metal wire)

bonded to the outer surface of the flange portion 162. The flange portion 162 preferably flares back over tubular portion 164 through which electrode 150 extends. The resilient sensor 158 can be made of an elastomeric solid polymer or foam made of materials described with respect to the corresponding component in FIG. 1. The metal foil strips 160 extend from an inner foil sleeve 166 which is maintained in tight engagement with the outer surface of the tubular electrode 150 by the tubular portion 164. The connecting element 168 has the structure, composition and function described with respect to the corresponding component of the embodiment shown in FIG. 1. It is critical that the foil 160 extend in an unbroken fashion from the sleeve 166 to maintain a secure, integral, noise-free connection. This electrode is inserted in the ear and connected with the audio signal generator and the auditory brainstem signal analyzer as described above with respect to the embodiment shown in FIG. 1.

The auditory signal generator and its associated magnetic field shielding can be of any standard type suitable for providing the auditory stimulation required for auditory brainstem response. The auditory sound generator is of standard construction well known in the art and is not an essential part of this invention.

A description of the procedures for measuring and analyzing auditory brainstem response is provided by "Physiological Mechanisms and Auditory Brainstem Evoked Response" by E. Borg, pp. 11–22 in the *Scandinavian Audiology Supplementum No.* 13, supra and "Auditory Evoked Potential Instrumentation: How to Choose", by Erickson et al, *Hearing Instruments*, Volume 32, No. 8, 1981, pp. 31–43, the entire contents of which are incorporated by reference. Included in the latter article is a description of the equipment currently available for making auditory brainstem response test analysis and ancillary equipment such as auditory signal generators.

A typical commercial auditory evoked potential system consists of units for stimulus presentation, signal detection, amplification and filtering, signal averaging, displaying data, hardcopying the data record and mass storage. The standard stimulus is a short-duration click produced by applying a square wave to the auditory signal generator with repetitions as high as 80 clicks per second. The evoked potential signal voltages detected by the electrode of this invention are extremely small in amplitude, and extraneous noise introduced amplification is removed by averaging. Filter settings are provided for optimum rejection of energy outside the frequency range of the evoked potential being recorded. The signal averager controls and senses the presentation of stimuli, collects the incoming signal and processes the data to form an averaged waveform. A display provides the operator with information regarding the averaged waveform and the input signal derived from the averaged signal. This can be a normalized display in which the summed data is divided by the number of repetitions. A means for producing a hardcopy of the data is convenient, and a digital mass data storage capability is important.

The growing interest in the auditory, evoked potential testing can be traced to the discovery of the auditory brainstem response recorded non-invasively from the human scalp. Subsequent research developed this test to provide a useful and versatile technique for evaluating hearing. It provides a means for examining patients who are difficult to test by behaviour means, efficiently discriminating between conductive and cochlear hearing disorders and differentiating peripheral and central pathology. Cochlear potentials of elevated magnitude indicate pressure in the inner ear. In some cases it can also reveal clinically asymptomatic lesions of the central pathways. The principal limitations derive from the high noise level in the electrical signal received from the skin surface. This noise level constitutes a serious impediment to full development of this testing means. Since the electrical signal being detected is typically less than one microvolt in amplitude, resistance or noise introduced at any point in the system causes a lower signal to noise ratio, seriously limiting the sensitivity of the device. Resistance introduced at the skin-electrode interface is very critical. To minimize this resistance, the conducting surface area in contact with the skin is maximized. Furthermore the selection of sensor metal and electrolytically conductive medium is important.

The ear electrode of this invention provides as greatly reduced skin-ear surface resistance and far greater sensitivity. The resistance has been reduced below 2 Kohm. Resistance as low as one Kohm has been achieved when the plastic foam is a continuously connecting cell polyurethane foam impregnated with an electrolytically conductive gel extending throughout the foam and making a good contact with the ear surface and tubular electrode conductor.

A high degree of safety and ease of insertion has been achieved. Risk of eardrum penetration has been eliminated even when the electrode is inserted by medical assistants with no special training in ear anatomy. The special guard, for example guard surface 32 in FIG. 3, limits insertion distance to a depth short of the eardrum.

The invention claimed is:

1. A non-invasive, external ear canal electrode comprising a conductive tube means for transmitting a sound stimulus to an ear canal and the tube means having a distal end, a resilient annular sensor means mounted on the distal end thereof for pressing outward against the inner surface of the ear canal and sensing electrical signals thereon, the annular sensor means having a resilient flared disk portion which extends radially outward beyond other elements at the distal end for contacting the ear canal surface, the flared disk portion having an outer conductive coating thereof and a tubular portion concentrically mounted on and engaging the conductive tube means, the conductive coating being in electrical contact with the conductive tube means.

2. The ear canal electrode of claim 1 wherein the distal end of the conductive tube means has a conductive flange in electrical contact with the outer conductive coating.

3. The ear canal electrode of claim 1 wherein the conductive tube means is a metal tube.

4. The ear canal electrode of claim 1 wherein the conductive tube means is a plastic tube having a conductive layer supported on the outer surface thereof.

5. The ear canal electrode of claim 1 wherein the conductive coating is a continuous conductive organic polymer layer covering said outer sensing means and an inner surface of the tubular portion in engagement with the conductive tube means.

6. The ear canal electrode of claim 5 wherein the conductive tube means is a plastic tube having a conductive layer supported on the outer surface thereof.

7. An ear canal electrode comprising a conductive tube means having an open distal end for transmitting electrical signals from the ear canal surface and for transmitting a sound stimulus to an ear canal, a resilient annular sensor means mounted on and surrounding the distal end thereof for resiliently pressing outwardly against the inner surface of the ear canal, the resilient annular sensor means having a conductive surface means for picking up electrical signals from the ear canal surface and for transmitting the electrical signals to the conductive tube means, wherein the resilient annular sensor means is a flared annular disk surrounding and mounted on the distal end of the conductive tube means.

8. An apparatus for testing hearing loss comprising an ear canal electrode in combination with a means for analyzing electrical signals picked up from the ear canal surface and transmitted by an ear canal electrode, the ear canal electrode comprising a conductive tube means having a distal end, an resilient annular sensor means mounted on the distal end thereof for contacting the ear canal surface and sensing electrical signals thereon, the annular sensor means having a resilient flange portion which extends radially outward beyond other elements at the distal end for pressing outwardly against the inner surface of the ear canal, the flange portion having an outer conductive coating thereon and a tubular portion concentrically mounted on and engaging the conductive tube means, the conductive coating being in electrical contact with the conductive tube means.

9. The apparatus for testing hearing loss of claim 8 wherein the conductive tube means comprises a means for transmitting a sound stimulus to an ear canal.

10. The apparatus for testing hearing loss of claim 9 wherein the distal end of the conductive tube means has conductive flange in electrical contact with the outer conductive coating.

11. The apparatus for testing hearing loss of claim 9 wherein the conductive tube means is a metal tube.

12. The apparatus for testing hearing loss of claim 9 wherein the conductive tube means is a plastic tube having a conductive layer supported on the outer surface thereof.

13. The apparatus for testing hearing loss of claim 9 wherein the conductive coating is a continuous conductive organic polymer layer covering said outer sensing means and an inner surface of the tubular portion in engagement with the conductive tube means.

14. The apparatus for testing hearing loss of claim 13 wherein the conductive tube means is a plastic tube having a conductive layer supported on the outer surface thereof.

15. An apparatus for testing hearing loss comprising an ear canal electrode in combination with a means for analyzing electrical signals picked up from the ear canal surface and transmitted by an ear canal electrode, the ear canal electrode comprising a conductive tube means having an open distal end for transmitting electrical signals from the ear canal surface and for transmitting a sound stimulus to an ear canal, a resilient annular sensor means mounted on and surrounding the distal end thereof for resiliently pressing outwardly against the inner surface of the ear canal, the resilient annular sensor means having a conductive surface means for picking up electrical signals from the ear canal surface and for transmitting the electrical signals to the conductive tube means.

16. The apparatus for testing hearing loss of claim 15 wherein the resilient annular sensor means is a flared annular disk surrounding and mounted on the distal end of the conductive tube means.

17. A method for diagnosing hearing defects comprising stimulating the auditory system of a person with bursts of sound waves issued from an ear canal electrode positioned in the ear canal of the person, detecting the electrical signals generated in response to the auditory system stimulation with the bursts of sound, the electrical signals being picked up from the ear canal surface with the ear canal electrode, and analyzing the electrical signals, wherein the ear canal electrode comprises a conductive tube means for transmitting a sound stimulus to an ear canal and having a distal end, a resilient annular sensor means mounted on the distal end thereof for contacting the ear canal surface and sensing electrical signals thereon, the annular sensor means having a resilient flange portion which extends radially outward beyond other elements at the distal end for pressing outwardly against the inner surface of the ear canal, the flange portion having an outer conductive coating thereof and a tubular portion concentrically mounted on and engaging the conductive tube means, the conductive coating being in electrical contact with the conductive tube means.

18. The method for diagnosing hearing defects of claim 17 wherein the distal end of the conductive tube means has a conductive flange in electrical contact with the outer conductive coating.

19. The method for diagnosing hearing defects of claim 17 wherein the conductive tube means is a metal tube.

20. The method for diagnosing hearing defects of claim 17 wherein the conductive tube means is a plastic tube having a conductive layer supported on the outer surface thereof.

21. The method for diagnosing hearing defects of claim 17 wherein the conductive coating is a continuous conductive organic polymer layer covering said outer sensing means and an inner surface of the tubular portion in engagement with the conductive tube means.

22. The method for diagnosing hearing defects of claim 21 wherein the conductive tube means is a plastic tube having a conductive layer supported on the outer surface thereof.

23. A method for diagnosing hearing defects comprising stimulating the auditory system of a person with bursts of sound waves issued from an ear canal electrode positioned in the ear canal of the person, detecting the electrical signals generated in response to the auditory system stimulation with the bursts of sound, the electrical signals being picked up from the ear canal surface with the ear canal electrode, and analyzing the electrical signals, wherein the ear canal electrode comprises a conductive tube means having an open distal end for transmitting electrical signals from the ear canal surface and for transmitting a sound stimulus to an ear canal, a resilient annular sensor means mounted on and surrounding the distal end thereof for resiliently pressing outwardly against the inner surface of the ear canal, the resilient annular sensor means having a conductive surface means for picking up electrical signals from the ear canal surface and for transmitting the electrical signals to the conductive tube means.

24. The method for diagnosing hearing defects of claim 23 wherein the resilient annular sensor means is a flared annular disk surrounding and mounted on the distal end of the conductive tube means.

* * * * *

UNITED STATES PATENT AND TRADEMARK OFFICE
CERTIFICATE OF CORRECTION

PATENT NO.   : 4,601,294
DATED        : July 22, 1986
INVENTOR(S)  : Hal C. Danby and Myron A. Beigler It is certified that error appears in the above-identified patent and that said Letters Patent is hereby corrected as shown below:

Col. 9, line 35 insert "a" after "has".

Signed and Sealed this

Thirty-first Day of March, 1987

Attest:

DONALD J. QUIGG

*Attesting Officer*      *Commissioner of Patents and Trademarks*